United States Patent
Xu et al.

(10) Patent No.: US 11,471,664 B2
(45) Date of Patent: Oct. 18, 2022

(54) BLOOD PUMP DEVICE

(71) Applicant: RocketHeart Technology Co. Ltd, Tianjin (CN)

(72) Inventors: Jian Xu, Tianjin (CN); Qinglin Fan, Tianjin (CN); Wenjin Wu, Tianjin (CN); Xuman Zhang, Tianjin (CN); Zhifu Han, Tianjin (CN); Guogang Song, Tianjin (CN); Ying Dai, Tianjin (CN)

(73) Assignee: RocketHeart Technology Co. Ltd, Tianjin (CN)

( * ) Notice: Subject to any disclaimer, the term of this patent is extended or adjusted under 35 U.S.C. 154(b) by 164 days.

(21) Appl. No.: 16/638,763

(22) PCT Filed: Sep. 18, 2017

(86) PCT No.: PCT/CN2017/102104
§ 371 (c)(1),
(2) Date: Feb. 13, 2020

(87) PCT Pub. No.: WO2019/041394
PCT Pub. Date: Mar. 7, 2019

(65) Prior Publication Data
US 2021/0128902 A1    May 6, 2021

(30) Foreign Application Priority Data

Aug. 29, 2017    (CN) .......................... 201710756110.4

(51) Int. Cl.
*A61M 60/416*    (2021.01)
*A61M 60/814*    (2021.01)
(Continued)

(52) U.S. Cl.
CPC ........ *A61M 60/416* (2021.01); *A61M 60/812* (2021.01); *A61M 60/814* (2021.01);
(Continued)

(58) Field of Classification Search
CPC .......... A61M 2210/125; A61M 60/122; A61M 60/148; A61M 60/205; A61M 60/40;
(Continued)

(56) References Cited

U.S. PATENT DOCUMENTS 5,211,546 A * 5/1993 Isaacson ............. A61M 60/824
                                                        417/356
5,216,308 A * 6/1993 Meeks ................ F16C 32/0459
                                                        310/90.5
(Continued)

FOREIGN PATENT DOCUMENTS

CN    102397598 A    4/2012
CN    205964586 U    2/2017
(Continued)

OTHER PUBLICATIONS

AU examination report dated Jan. 14, 2021 in AU application No. 2017430315.

*Primary Examiner* — Kenneth Bomberg
*Assistant Examiner* — Adam W Brown
(74) *Attorney, Agent, or Firm* — Gang Yu

(57) ABSTRACT

Disclosed is a blood pump device. The blood pump device includes: a housing having an overflow passage, and an inlet and an outlet respectively connected to the overflow passage; a rotor assembly rotatably disposed in the overflow passage; a coil disposed in a side wall of the housing; a first permanent magnet portion disposed inside the rotor assembly; a second permanent magnet portion disposed in the side wall of the housing, the first permanent magnet portion and the second permanent magnet portion forming a radial permanent magnet bearing; a piece of electric motor magnetic steel disposed inside a rotor of the rotor assembly; and a magnetic protection portion disposed at a periphery of the coil, wherein the magnetic protection portion and the elec- (Continued)

tric motor magnetic steel act together to provide an axial pre-tightening force for the rotor assembly.

15 Claims, 4 Drawing Sheets

(51) Int. Cl.
  *A61M 60/812* (2021.01)
  *A61M 60/82* (2021.01)
  *F04D 7/00* (2006.01)
  *F04D 13/06* (2006.01)
  *F04D 29/18* (2006.01)

(52) U.S. Cl.
  CPC ............... *A61M 60/82* (2021.01); *F04D 7/00* (2013.01); *F04D 13/06* (2013.01); *F04D 29/18* (2013.01)

(58) Field of Classification Search
  CPC ............. A61M 60/416; A61M 60/812; A61M 60/814; A61M 60/82; F04D 13/06; F04D 29/041; F04D 29/048; F04D 29/18; F04D 29/186; F04D 7/00
  See application file for complete search history.

(56) References Cited

U.S. PATENT DOCUMENTS

| | | | |
|---|---|---|---|
| 5,695,471 A * | 12/1997 | Wampler | H02K 7/09 604/131 |
| 5,840,070 A * | 11/1998 | Wampler | F16C 39/063 604/131 |
| 6,201,329 B1 * | 3/2001 | Chen | A61M 60/148 310/90.5 |
| 6,290,640 B1 * | 9/2001 | Goldowsky | F04B 17/046 600/16 |
| 6,293,901 B1 | 9/2001 | Prem | |
| 6,866,625 B1 * | 3/2005 | Ayre | A61M 60/205 600/16 |
| 7,229,258 B2 * | 6/2007 | Wood | A61M 60/148 417/355 |
| 7,462,019 B1 * | 12/2008 | Allarie | A61M 60/82 417/423.12 |
| 8,002,518 B2 * | 8/2011 | Woodard | A61M 60/824 415/104 |
| 9,144,638 B2 * | 9/2015 | Zimmermann | F16C 17/10 |
| 9,265,870 B2 * | 2/2016 | Reichenbach | A61M 25/005 |
| 9,308,304 B2 * | 4/2016 | Peters | A61M 60/205 |
| 10,660,996 B2 * | 5/2020 | Foster | A61M 60/82 |
| 10,780,207 B2 * | 9/2020 | Dur | A61M 60/419 |
| 2009/0259308 A1 | 10/2009 | Hidaka et al. | |
| 2011/0237863 A1 * | 9/2011 | Ricci | A61M 60/82 600/16 |
| 2019/0046704 A1 * | 2/2019 | Choub | F04D 13/024 |
| 2020/0368415 A1 * | 11/2020 | Antaki | F16C 32/0425 |

FOREIGN PATENT DOCUMENTS

| | | | | |
|---|---|---|---|---|
| CN | 206285301 U | 6/2017 | | |
| EP | 2292282 A1 | 3/2011 | | |
| WO | 2005030296 A2 | 4/2005 | | |
| WO | 2009126523 A1 | 10/2009 | | |
| WO | WO-2016187057 A1 * | 11/2016 | | A61M 60/82 |

* cited by examiner

BLOOD PUMP DEVICE

CROSS-REFERENCE TO RELATED APPLICATION(S)

The present disclosure is a national stage application of International Patent Application No. PCT/CN2017/102104, which is filed on Sep. 18, 2017 and claims priority to Chinese Patent Application No. 201710756110.4, filed on Aug. 29, 2017 and entitled "Blood Pump Device", the contents of which are hereby incorporated by reference in its entirety.

TECHNICAL FIELD

The disclosure relates to a technical field of medical equipment, in particular to a blood pump device.

BACKGROUND

In a related art, Heart Failure (HF) is colloquially known as the natural heart does not pump enough blood to maintain blood circulation throughout the body. According to WTO (World Health Organization) statistics, about 15% to 20% of people suffer from different degrees of heart failure, over the age of 65, more than 50% of all hospital admissions are due to heart failure, and at the same time, the case fatality rate after 5 years exceeds 50%. For patients with heart failure, there are only three treatment approaches, namely conservative drug therapy, heart transplantation and direct mechanical ventricular assistance. The drug therapy is less effective, the heart transplantation is very difficult because of donor limitations, so a Ventricular Assist Device (VAD) has become the universally recognized most effective treatment approach for all kinds of terminal heart failure. The main component of the VAD is a blood pump. An inflow tube of the blood pump is generally connected with a left or right ventricle of the human heart, and an outflow tube is connected with an aorta or pulmonary artery, and the pump is connected with a control driver (with a power supply device). The control driver controls the blood pump to output blood with a certain pressure (generally 80-120 mmHg) and a certain flow rate (generally 2-10 L/min) to share a power demand of normal human activities for the human heart. The VAD is divided into a Left VAD (LVAD), a Right VAD (RVAD) and Bi-Ventricular Assist Device (BiVAD) depending on where the blood pump assists the heart. Gradually developing from the earliest pulsating blood pump to the existing rotary continuous blood pump, the blood pump has been applied from the lab to the clinic in Europe and the United States. The first-generation pulsating blood pump is approved by FDA for Bridge-To-Transplant (BTT) in 1994. The DeBakey axial-flow LVAD is the first rotary blood pump to conduct clinical trials in Europe and the United States, the HeartMate II is the first rotary blood pump approved by FDA for BTT in 2008. The common Jarvik2000 and HeartMate II adopt a mechanical bearing to provide support, the HeartWare adopts a combination of a liquid bearing and a permanent magnet bearing to provide support, and the HeartMate III and the DuraHeart adopt active magnetic levitation support.

At present, the rotary blood pump is generally divided into two main components which are a housing and an impeller rotor. Support bearings of the impeller rotor in the housing may be divided into several types which are mechanical bearing, hydrodynamic bearing, and active or passive magnetic levitation bearing. The mechanical bearing runs stably but is prone to thrombosis and wear. The hydrodynamic bearing acts only in the case of high-speed rotation of a rotor, which limits a speed regulation range of the blood pump. The volume and power consumption of the active magnetic levitation bearing increase relatively due to the introduction of a sensor. The passive magnetic levitation bearing cannot achieve stable suspension with full degrees of freedom, and must be used in conjunction with other forms of bearings.

In a related art, a rotary blood pump is disclosed in Patent Application No. CN206285301U. The rotary blood pump provides a suspension force for a rotor by means of a magnetic levitation bearing, and a magnetic line of force generated by a coil leaks easily, so an efficiency of an electric motor is low; in addition, the blood pump provides both an axial pre-tightening force and a radial support by means of a radial permanent magnet bearing, so the size of the blood pump is large, and the reliability is low.

SUMMARY

Some embodiments of the disclosure provide a blood pump device. The blood pump device provides a radial support force for a rotor assembly by using a radial permanent magnet bearing, and provides an axial pre-tightening force for the rotor assembly by means of a combined action of a magnetic protection portion and a piece of electric motor magnetic steel, so as to support the rotor assembly in an axial direction by means of the combined action of a flow guiding vane.

Some embodiments of the disclosure provide a blood pump device. The blood pump device includes: a housing having an overflow passage, and an inlet and an outlet respectively connected to the overflow passage; a rotor assembly rotatably provided in the overflow passage; a coil disposed in a side wall of the housing; a first permanent magnet portion disposed inside the rotor assembly; a second permanent magnet portion disposed in the side wall of the housing, the first permanent magnet portion and the second permanent magnet portion forming a radial permanent magnet bearing; an electric motor magnetic steel disposed inside a rotor of the rotor assembly; and a magnetic protection portion disposed at a periphery of the coil. The magnetic protection portion and the electric motor magnetic steel act together to provide an axial pre-tightening force for the rotor assembly.

In an exemplary embodiment, the housing is provided with a central axis. In a direction parallel to the central axis, there is a space H between an end face, close to the inlet, of the electric motor magnetic steel and an end face, close to the inlet, of the magnetic protection portion, so as to provide the axial pre-tightening force for the rotor assembly by means of a combined action of the magnetic protection portion and the electric motor magnetic steel.

In an exemplary embodiment, the blood pump device further includes a space between an end face, away from the inlet, of the electric motor magnetic steel and an end face, away from the inlet, of the magnetic protection portion; or an end face, away from the inlet, of the electric motor magnetic steel is flush with an end face, away from the inlet, of the magnetic protection portion.

In an exemplary embodiment, the housing includes: a sleeve including a sleeve body and an inner through hole, the rotor assembly being located in the inner through hole; and a volute connected with the sleeve, the volute being used for collecting and rectifying blood flowing through the sleeve, and having a cavity connected to the inner through hole. The inner through hole and the cavity form the overflow passage, the inlet is disposed on the sleeve, the outlet is disposed on the volute, and there is an included angle between a centerline of the inlet and a centerline of the outlet.

In an exemplary embodiment, the blood pump device further includes a first cone structure disposed in the cavity of the volute, and there is a space between the first cone structure and the rotor assembly, so that an extreme position of an axial movement of the rotor assembly is limited and the first cone structure is configured to rectify and centrifuge a fluid flowing through the sleeve.

In an exemplary embodiment, both the magnetic protection portion and the second permanent magnet portion are disposed on a side wall of the sleeve. The blood pump device further includes: a first non-magnetic portion disposed inside a rotor (23) of the rotor assembly; and a second non-magnetic portion disposed inside the side wall of the sleeve. In a flowing direction of fluid, the first non-magnetic portion, the electric motor magnetic steel and the first permanent magnet portion are sequentially disposed at intervals, and the second non-magnetic portion, the coil and the second permanent magnet portion are sequentially disposed at intervals.

In an exemplary embodiment, a side wall of the sleeve includes an inner wall and an outer wall disposed with the inner wall at interval. An annular space is formed between the inner wall and the outer wall, and the coil, the magnetic protection portion and the second permanent magnet portion are disposed in the annular space.

In an exemplary embodiment, the blood pump device further includes a flow guiding structure disposed in the overflow passage; the flow guiding structure is located at the inlet. A second cone structure cooperating with the flow guiding structure is disposed on an end face, facing to the flow guiding structure, of the rotor assembly.

In an exemplary embodiment, the flow guiding structure includes a plurality of flow guiding vanes, and the plurality of flow guiding vanes are disposed at intervals on an inner wall of a sleeve of the housing in a circumferential direction.

In an exemplary embodiment, in a flowing direction of fluid, an end face, close to the inlet, of the first permanent magnet portion is flush with an end face, close to the inlet, of the second permanent magnet portion, and the end face, away from the inlet, of the first permanent magnet portion is flush with an end face, away from the inlet, of the second permanent magnet portion.

In an exemplary embodiment, the rotor assembly includes a rotor and one or a plurality of vanes disposed on the rotor. When the rotor assembly includes the plurality of vanes, the plurality of vanes are disposed at intervals around a circumferential direction of the rotor.

In an exemplary embodiment, the magnetic protection portion is made of a soft magnetic material.

By using the technical solutions of the embodiments of the disclosure, the radial support force is provided for the rotor assembly by using the radial permanent magnet bearing, and the axial pre-tightening force is provided for the rotor assembly by means of the combined action of the magnetic protection portion and the electric motor magnetic steel, so as to support the rotor assembly in the axial direction by means of the combined action of the flow guiding vane; in such a manner, compared to using an axial offset of a magnetic ring to generate the axial pre-tightening force in the art known to the inventors, a greater axial acting force is provided by using the electric motor magnetic steel and the magnetic protection portion in some embodiments of the disclosure, and for the magnetic rings with the same size, the smaller the axial offset, the greater the radial stiffness, so the whole blood pump device has reduced length, more compact structure, and higher radial stability.

BRIEF DESCRIPTION OF THE DRAWINGS

The accompanying drawings constituting a part of the disclosure are used for providing further understanding of the disclosure. Schematic embodiments of the disclosure and description thereof are used for illustrating the disclosure and not intended to form an improper limit to the disclosure. In the accompanying drawings.

The above accompanying drawings include the following reference numbers:

10, housing; 11, overflow passage; 12, inlet; 13, outlet; 14, volute; 141, bottom wall; 15, first cone structure; 16, sleeve; 20, rotor assembly; 21, third cone structure; 23, rotor; 22, second cone structure; 30, coil; 31, magnetic protection portion; 40. electric motor magnetic steel; 41. third permanent magnet portion; 42, first permanent magnet portion; 43, fourth permanent magnet portion; 44, second permanent magnet portion; 45, first non-magnetic portion; 46, second non-magnetic portion; 50, flow guiding structure; 60, wire.

DETAILED DESCRIPTION OF THE EMBODIMENTS

It is to be noted that the embodiments in the disclosure and the characteristics in the embodiments may be combined under the condition of no conflicts. The disclosure is elaborated below with reference to the accompanying drawings and embodiments.

To solve the problem in the blood pump device known to the inventors that using a radial permanent magnet bearing to provide a radial support force and an axial pre-tightening force for a rotor assembly results in a longer length and a larger volume of a blood pump device, the disclosure improves the structure of the blood pump device, as specifically described below.

Embodiment 1

Figure 1:
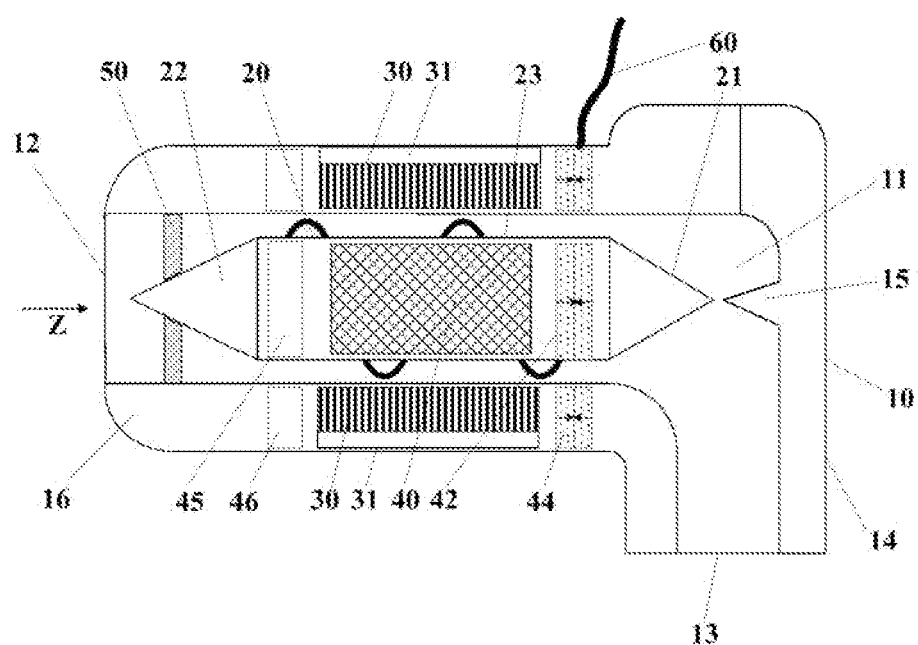
FIG. 1 illustrates a structure diagram of a blood pump device according to embodiment 1 of the disclosure.
Figure 3:
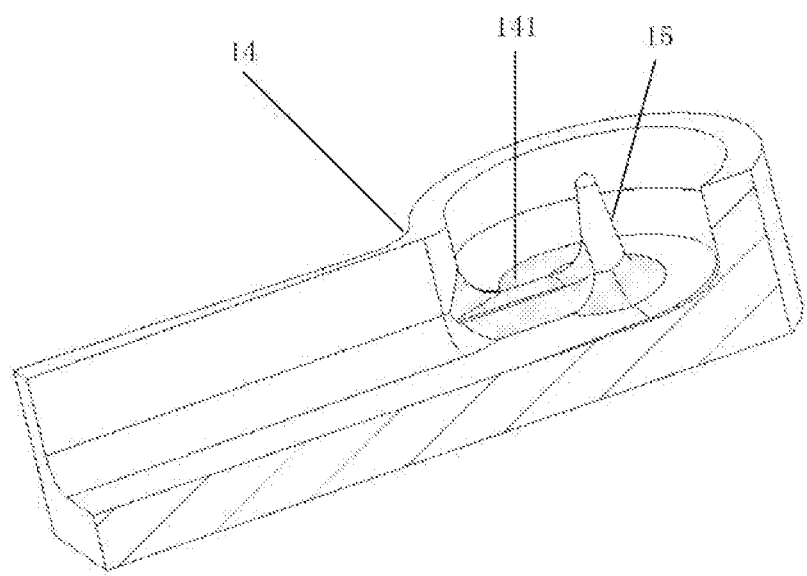
FIG. 3 illustrates a structure diagram of embodiment 1 of a volute of the blood pump device in FIG. 1.
Figure 4:
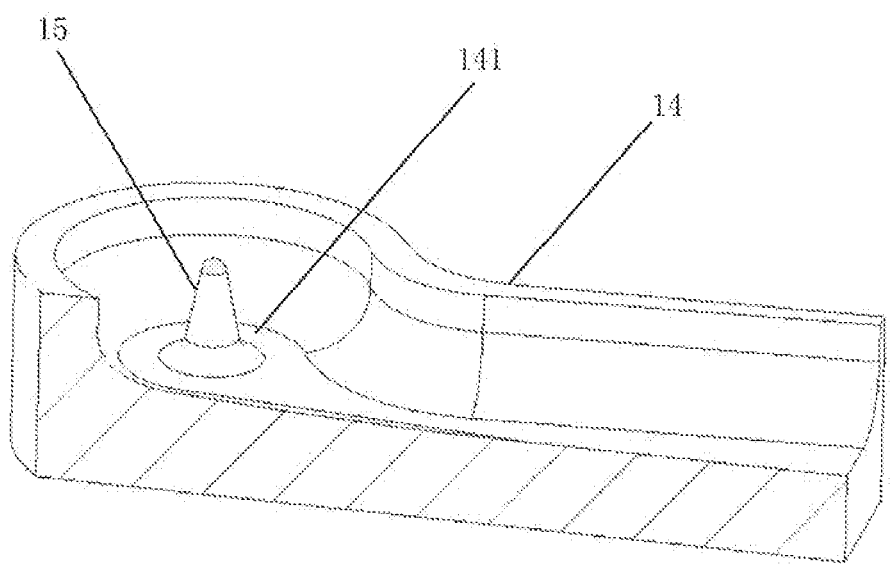
FIG. 4 illustrates a structure diagram of embodiment 2 of a volute of the blood pump device in FIG. 1.

As shown in FIG. 1, FIG. 3 and FIG. 4, a blood pump device of embodiment 1 includes a housing 10, a rotor assembly 20, a coil 30, an electric motor magnetic steel 40, a first permanent magnet portion 42 provided inside the rotor assembly 20, and a second permanent magnet portion 44 provided in a side wall of the housing 10. The housing 10 has an overflow passage 11, and an inlet 12 and an outlet 13 respectively connected to the overflow passage 11. The rotor assembly 20 is rotatably disposed in the overflow passage 11. The coil 30 is disposed in the side wall of the housing 10. The electric motor magnetic steel 40 is disposed inside the rotor assembly 20. In some embodiments of the present disclosure, the blood pump device further includes a magnetic protection portion 31. The magnetic protection portion 31 is disposed at a periphery of the coil 30. The magnetic protection portion 31 and the electric motor magnetic steel 40 act together to provide an axial pre-tightening force for the rotor assembly 20.

With the above setting, some embodiments of the disclosure provide a radial acting force, which enables the rotor assembly 20 to suspend in an equilibrium position, for the rotor assembly 20 by means of a radial permanent magnet bearing, and provides the axial pre-tightening force for the rotor assembly 20 by means of a combined action of the magnetic protection portion 31 and the electric motor magnetic steel 40. In this way, providing radial support and axial support for the rotor assembly 20 through different structural components is able to provide a greater axial pre-tightening force for the rotor assembly 20 on one hand, and make the radial support more reliable on the other hand. In the related art, only the radial permanent magnet bearing is used to provide both the radial support force and the axial pre-tightening force for the rotor assembly 20, and for magnetic rings with the same size, the smaller the axial offset, the greater the radial stiffness, so the axial offset of the magnetic ring forming the radial permanent magnet bearing will be very small for improving the radial stiffness, which is difficult to provide a relatively great axial pre-tightening force for the rotor assembly; if a relatively great axial pre-tightening force is to be provided, it is necessary to increase the axial offset of the magnetic ring, so a length of the whole blood pump device will be increased, and the radial support force is not stable enough. The technical solutions of some embodiments of the disclosure, solving the above disadvantages of the related art, not only make the length of the pump smaller and make the structure more compact, but also provide a more stable radial support force for the rotor assembly 20.

In some embodiments, the magnetic protection portion 31 is disposed in a side wall of the housing 10. In a saturation magnetization range of material of the magnetic protection portion 31, a magnetic line of force generated by the coil 30 will form a closed loop inside the magnetic protection portion 31, so there is no magnetic leakage. Because a rotary motion of the rotor assembly 20 is generated under the combined action of the coil 30 and the electric motor magnetic steel 40, through the above setting, an utilization ratio of the magnetic line of force of the coil 30 and the electric motor magnetic steel 40 is improved, thereby improving a working efficiency of the electric motor magnetic steel 40; in addition, by adjusting a magnitude of a current or a voltage supplied to the coil 30, a rotation speed of the rotor assembly 20 is adjusted in a wide range, so as to output different flow pressures to adapt to demands of different patients.

In some embodiments, the magnetic protection portion 31 is made of a soft magnetic material. The soft magnetic material means that when magnetization occurs at Hc, a magnetic field intensity is not greater than 1000 A/m, and such material becomes a soft magnet. In general, the soft magnetic material is iron-silicon alloy and various soft magnetic ferrites. In an embodiment, the magnetic protection portion 31 is made of magnet. Because the magnetic protection portion 31 is a soft magnetic material magnetic permeability of which is much higher than that of air, no matter in an internal magnetic field or an external magnetic field, the magnetic line of force inside the blood pump device will form a closed loop inside the magnetic protection portion 31 within the saturation magnetization range of material of the magnetic protection portion 31, so there is no magnetic leakage. In some embodiments, the magnetic protection portion 31 is an axial sleeve, and the coil 30 is disposed inside the axial sleeve.

In some embodiments, the rotor assembly 20 includes a rotor 23 and one or more vanes disposed on the rotor 23. When the rotor assembly 20 includes a plurality of vanes, the plurality of vanes 23 are disposed at intervals around a circumferential direction of the rotor 23. In some embodiments, each of the plurality of vanes is spiral, and a spiral vane extends in an axial direction of the rotor 23. The rotation of the vane can pump in blood from the inlet 12, and after the blood flows through the overflow passage 11, pump out the blood from the outlet 13 with a certain pressure and flow; besides, the damage to the blood is less after the vane is disposed.

In embodiment 1, the blood pump device further includes a controller and a wire 60 connected with the controller. The rotary motion of the rotor assembly 20 is generated under the combined action of the coil 30 in the housing 10 and the electric motor magnetic steel 40 in the rotor assembly 20. A control drive signal is input through the wire 60. The rotation speed of the rotor assembly 20 is adjusted in a wide range, so as to output different flow pressures.

As shown in FIG. 1, in embodiment 1 of the disclosure, the housing 10 has a central axis. In a direction parallel to the central axis, there is a space H between an end face, close to the inlet 12, of the electric motor magnetic steel 40 and an end face, close to the inlet 12, of the magnetic protection portion 31, so as to provide the axial pre-tightening force for the rotor assembly 20 by means of the combined action of the magnetic protection portion 31 and the electric motor magnetic steel 40.

In some embodiments, the magnetic protection portion 31 is a soft magnetic material, the electric motor magnetic steel 40 is a hard magnetic material, and a magnetic force of attraction is generated between them. When the electric motor magnetic steel 40 is at a center of the magnetic protection portion 31 in an axial direction of the magnetic protection portion 31, that is, a central axis of the electric motor magnetic steel 40 overlaps with a central axis of the magnetic protection portion 31, an axial magnetic force between them is 0.

As shown in FIG. 1, a position of the electric motor magnetic steel 40 is closer to a positive direction of Z axis than the magnetic protection portion 31, and then the magnetic protection portion 31 generates an attractive force, which makes the rotor assembly 20 face towards a negative direction of Z axis, to the rotor assembly 20, namely provides the axial pre-tightening force for the rotor assembly 20, so that the rotor assembly 20 maintains a stable suspended state in an axial direction. At the same time, if a position of the rotor assembly 20 is offset by an axial impact force, the axial pre-tightening force ensures the rotor assembly 20 to return to an original position after the axial impact force disappears.

As shown in FIG. 1, in embodiment 1 of the disclosure, there is a space between an end face, away from the inlet 12, of the electric motor magnetic steel 40 and an end face, away from the inlet 12, of the magnetic protection portion 31.

In embodiment 1 of the disclosure, there is a space H between the end face, close to the inlet 12, of the electric motor magnetic steel 40 and an end face, close to the inlet 12, of the magnetic protection portion 31, and there is the space between the end face, away from the inlet 12, of the electric motor magnetic steel 40 and an end face, away from the inlet 12, of the magnetic protection portion 31, that is, the electric motor magnetic steel 40 and the magnetic protection portion 31 are offset in the axial direction, so the electric motor magnetic steel 40 is inside the magnetic protection portion 31 and does not protrude out of the two opposite end faces of the magnetic protection portion 31. With the above setting, the electric motor magnetic steel 40 and the magnetic protection portion 31 act together to provide the axial pre-tightening force towards the negative direction of Z axis for the rotor assembly 20.

In this way, an enough axial pre-tightening force is provided for the rotor assembly 20 by means of the combined action of the magnetic protection portion 31 and the electric motor magnetic steel 40, so it is not needed to generate the axial pre-tightening force and the axial support by means of the axial offset of the magnetic ring as in the art known to the inventors, which is difficult to ensure radial stability and provide an enough axial pre-tightening force at the same time. The radial permanent magnet bearing of the blood pump in the some embodiments of the disclosure provides the radial stiffness, and the radial support is more stable; besides, the blood pump device in an embodiment of the disclosure has a smaller length and a more compact structure.

Certainly, in some embodiments not described in the disclosure, the end face, away from the inlet 12, of the electric motor magnetic steel 40 is flush with the end face, away from the inlet 12, of the magnetic protection portion 31.

As shown in FIG. 1, in an embodiment of the disclosure, the housing 10 includes a sleeve 16 and a volute 14. The sleeve 16 includes a sleeve body and an inner through hole. The rotor assembly 20 is located in the inner through hole. The volute 14 is connected with the sleeve 16. The volute 14 is used for collecting and rectifying the blood flowing through the sleeve 16. The volute 14 has a cavity connected to the inner through hole. The inner through hole of the sleeve 16 and the cavity form the overflow passage 11. The inlet 12 is disposed on the sleeve 16, and the outlet 13 is disposed on the volute 14. An included angle is disposed between a centerline of the inlet 12 and a centerline of the outlet 13.

With the above setting, the housing 10 has both advantages of an axial flow pump and advantages of a centrifugal pump in an art known to the inventors, that is, the blood pump device in the disclosure is a mixed-flow pump, which not only speeds up the blood entering the housing 10 from the inlet 12, but also changes a flowing direction of the blood flowing out from the outlet 13; at the same time, the blood pump device combines the advantage of small diameter of the axial flow pump and the advantage of rectifying a flow pressure curve of the centrifugal pump, so it better meets the physiological requirements of the human body. As shown in FIG. 1, in some embodiments of the disclosure, a first cone structure 15 is disposed in the cavity of the volute 14. The first cone structure 15 and the rotor assembly 20 are arranged correspondingly to limit an extreme position of axial movement of the rotor assembly 20, and there is a space between the first cone structure 15 and the rotor assembly 20 in a flowing direction of fluid.

With the above setting, the first cone structure 15 enables, because of its cone characteristic, the rotor assembly 20 which offsets towards the positive direction of Z axis due to an axial impact automatically center, which not only acts in limiting, but also plays a function of centrifugally rectifying to rectify and centrifuge the fluid flowing through the sleeve 16.

In some embodiments, an end, facing towards the volute 14, of the rotor 23 of the rotor assembly 20 is provided with a third cone structure 21. The first cone structure 15 and the third cone structure 21 are provided correspondingly, so the extreme position of axial movement of the whole rotor assembly 20 is limited on one hand, and the fluid flowing through the sleeve 16 is rectified and centrifuged on the other hand. In addition, an adequate clearance is provided between the first cone structure 15 and the third cone structure 21, so after they contact, a direction of the axial pre-tightening force is still along the negative direction of Z axis.

As shown in FIG. 1, in the flowing direction of fluid, an end face, close to the inlet 12, of the first permanent magnet portion 42 is flush with an end face, close to the inlet 12, of the second permanent magnet portion 44, and an end face, away from the inlet 12, of the first permanent magnet portion 42 is flush with an end face, away from the inlet 12, of the second permanent magnet portion 44. So, the radial permanent magnet bearing formed by the first permanent magnet portion 42 and the second permanent magnet portion 44 only provides the radial support for the rotor assembly 20.

In some embodiments not described in the drawings of the disclosure, the first permanent magnet portion 42 and the second permanent magnet portion 44 are offset in the axial direction (there is a space between the end face, away from the inlet, of the first permanent magnet portion 42 and the end face, away from the inlet, of the second permanent magnet portion 44), that is, the first permanent magnet portion 42 is closer to the inlet 12 with respect to the second permanent magnet portion 44.

As shown in FIG. 3, the volute 14 includes a bottom wall 141 and a side wall connected with the bottom wall 141. The first cone structure 15 is disposed on the bottom wall 141, and a surface, facing towards the rotor assembly 20, of the bottom wall 141 is arranged inclined. The surface spirally descents around the first cone structure 15, so after the blood flowing through the sleeve 16 enters the volute 14, the surface plays a role of buffering and rectifying, so that the flow pressure curve changes more gently when the fluid entering the blood pump and flowing in the axial direction of the sleeve 16 is spun out after being centrifuged at the volute 14 to change the direction.

FIG. 4 shows a structure diagram of another embodiment of the volute 14. The difference between FIG. 4 and FIG. 3 is that the surface, facing towards the rotor assembly 20, of the bottom wall 141 of the volute 14 is a plane.

As shown in FIG. 1, in embodiment 1 of the disclosure, both the magnetic protection portion 31 and the second permanent magnet portion 44 are disposed in the side wall of the sleeve 16. The blood pump device further includes a first non-magnetic portion 45 and a second on-magnetic portion 46. The first non-magnetic portion 45 is disposed inside the rotor 23 of the rotor assembly 20, and the second on-magnetic portion 46 is disposed in the side wall of the sleeve 16. In the flowing direction of fluid, the first non-magnetic portion 45, the electric motor magnetic steel 40 and the first permanent magnet portion 42 are sequentially disposed at intervals; and the second non-magnetic portion 46, the coil 30 and the second permanent magnet portion 44 are sequentially disposed at intervals.

In some embodiments, there are two groups of permanent magnet rings disposed in the first permanent magnet portion 42, there are two groups of permanent magnet rings disposed in the second permanent magnet portion 44, and there is no permanent magnet ring disposed in the first non-magnetic portion 45, there is no permanent magnet ring disposed in the second non-magnetic portion 46. The permanent magnet rings in the first permanent magnet portion 42 and the second permanent magnet portion 44 interact to form the radial permanent magnet bearing, which provides an axial force for the rotor assembly 20, thereby ensuring the radial stiffness of the rotor assembly 20 to enable the rotor assembly 20 to suspend in an equilibrium position. With the above setting, on the premise of ensuring a normal operation of the rotor assembly 20, the assembled structure is simpler and the weight is lighter. The terms of the first non-magnetic portion 45 and the second non-magnetic portion 46 are used for emphasizing that there is no magnetic ring arranged on a front end of the coil 30 of the blood pump device in FIG. 2, and there is no magnetic ring arranged on a front end of the electric motor magnetic steel 40.

Certainly, in some embodiments not described in the drawings of the disclosure, it is also possible to adopt, according to actual needs, three or more groups of permanent magnet rings to interact, so as to provide the radial stiffness for the rotor assembly 20.

As shown in FIG. 1, in embodiment 1 of the disclosure, the side wall of the sleeve 16 includes an inner wall and an outer wall provided with the inner wall at interval; there is an annular space formed between the inner wall and the outer wall, and the coil 30, the magnetic protection portion 31 and the second permanent magnet portion 44 are disposed in the annular space.

The above setting is simple in structure and easy to process.

As shown in FIG. 1, in embodiment 1 of the disclosure, the blood pump device further includes a flow guiding structure 50 disposed in the overflow passage 11. The flow guiding structure 50 is located at the inlet. A second cone structure 22 cooperating with the flow guiding structure 50 is disposed on an end face, facing to the flow guiding structure 50, of the rotor assembly 20.

Specifically, the flow guiding structure 50 rectifies the blood flowing in from the inlet, and supports the rotor assembly 20. In this way, the radial acting force, which enables the rotor assembly 20 to suspend in the equilibrium position, is provided for the rotor assembly 20 by means of the radial permanent magnet bearing, the axial pre-tightening force is provided for the rotor assembly 20 by means of the combined action of the magnetic protection portion 31 and the electric motor magnetic steel 40, and the support force is provided for the rotor assembly 20 through the flow guiding structure 50. So, providing the radial support and the axial support for the rotor assembly 20 by means of different structural components in the technical solution of the embodiment provides the greater axial pre-tightening force for the rotor assembly 20 on one hand, and makes the radial support more reliable on the other hand.

As shown in FIG. 1, in some embodiments of the disclosure, the flow guiding structure 50 includes a plurality of flow guiding vanes, and the plurality of vanes are disposed on the inner wall of the sleeve 16 at intervals around a circumferential direction.

In the embodiments, after the blood pump device is used for several years, wear will occur on a contact surface between each of the flow guiding vanes and the second cone structure 22. Due to structure features of the second cone structure 22 and the existence of the axial pre-tightening force, the rotor assembly 20 and the each of the flow guiding vanes will automatically pre-tighten, thereby avoiding the disadvantage that the blood pump adopting mechanical bearings at two ends needs to be added with an elastic pre-tightening element, and reducing a failure risk. The number of the flow guiding vanes is 2 or 3 or 4, etc., and the flow guiding vanes do not make a whole circle. When the rotor assembly rotates, a certain amount of blood cells accumulate on the contact surface of the second cone structure 22 and the each of the flow guiding vanes; but with the rotation, the contact surface of the second cone structure 22 and the each of the flow guiding vanes will become a non-contact surface, and the accumulated blood cells will also be washed away by the blood flowing through the non-contact surface, thereby avoiding the problem that the common mechanical bearing is prone to thrombosis.

Embodiment 2

In embodiment 2 of the disclosure, the difference between embodiment 2 and embodiment 1 is as follows.

Figure 2:
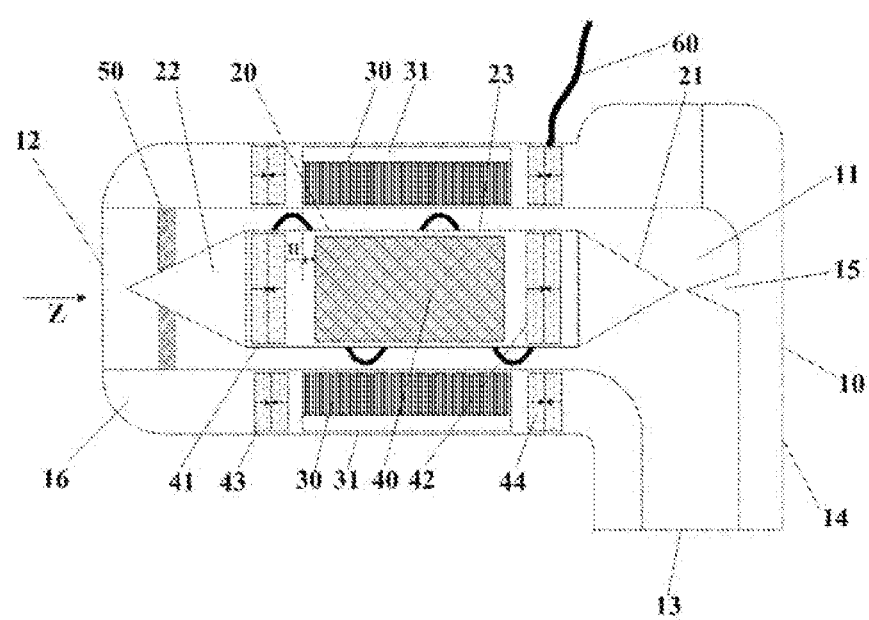
FIG. 2 illustrates a structure diagram of a blood pump device according to embodiment 2 of the disclosure.

As shown in FIG. 2, there is no first non-magnetic portion 45 and second non-magnetic portion 46 provided in embodiment 2, but the third permanent magnet portion 41 and the fourth permanent magnet portion 43 are provided. In the flowing direction of fluid, namely the direction shown in FIG. 2, the third permanent magnet portion 41, the electric motor magnetic steel 40 and the first permanent magnet portion 42 are sequentially disposed at intervals; and the fourth permanent magnet portion 43, the coil 30 and the second permanent magnet portion 44 are sequentially disposed at intervals. Both the third permanent magnet portion 41 and the fourth permanent magnet portion 43 include two groups of permanent magnet rings.

Certainly, in some embodiments not described in the drawings of the disclosure, the third permanent magnet portion 41 and the fourth permanent magnet portion 43 adopts, according to actual needs, three or more groups of permanent magnet rings to interact, so as to provide the radial stiffness for the rotor assembly 20.

Other structures of embodiment 2 are the same as embodiment 1, and will not be repeated here.

The above is only some embodiments of the disclosure and not intended to limit the disclosure; for those skilled in the art, the disclosure may have various modifications and changes. Any modifications, equivalent replacements, improvements and the like within the spirit and principle of the disclosure should fall within the protection scope of the claims of the disclosure.

What is claimed is:
1. A blood pump device, comprising:
a housing having an overflow passage, and an inlet and an outlet respectively connected to the overflow passage;
a rotor assembly rotatably provided in the overflow passage;
a coil disposed in a side wall of the housing;
a first permanent magnet portion disposed inside the rotor assembly;
a second permanent magnet portion disposed in the side wall of the housing, the first permanent magnet portion and the second permanent magnet portion forming a radial permanent magnet bearing;
an electric motor magnetic steel disposed inside the rotor assembly; and
a magnetic protection portion disposed at a periphery of the coil, wherein the magnetic protection portion and the electric motor magnetic steel act together to provide an axial pre-tightening force for the rotor assembly; the magnetic protection portion is an axial sleeve;
wherein the housing comprises:
a sleeve comprising a sleeve body and an inner through hole, the rotor assembly being located in the inner through hole; and a volute connected with the sleeve, the volute being used for collecting and rectifying blood flowing through the sleeve, and having a cavity connected to the inner through hole;

wherein the inner through hole and the cavity form the overflow passage, the inlet is disposed on the sleeve, the outlet is disposed on the volute, and there is an included angle between a centerline of the inlet and a centerline of the outlet;

wherein the blood pump device further comprises a first cone structure disposed in the cavity of the volute, and there is a space between the first cone structure and the rotor assembly, so that an extreme position of an axial movement of the rotor assembly is limited and the first cone structure is configured to rectify and centrifuge a fluid flowing through the sleeve;

an end, facing towards the volute, of the rotor is provided with a third cone structure, the first cone structure and the third cone structure are provided correspondingly; the volute comprises a bottom wall and a side wall connected with the bottom wall, the first cone structure is disposed on the bottom wall, and a surface, facing towards the rotor assembly, of the bottom wall is inclined.

2. The blood pump device as claimed in claim 1, wherein the housing is provided with a central axis; in a direction parallel to the central axis, there is a space H between an end face of the electric motor magnetic steel facing the inlet and an end face of the magnetic protection portion facing the inlet, so as to provide the axial pre-tightening force for the rotor assembly by means of a combined action of the magnetic protection portion and the electric motor magnetic steel.

3. The blood pump device as claimed in claim 2, wherein the blood pump device further comprises a space between an end face of the electric motor magnetic steel away from the inlet and an end face of the magnetic protection portion away from the inlet; or an end face of the electric motor magnetic steel away from the inlet is flush with an end face of the magnetic protection portion away from the inlet.

4. The blood pump device as claimed in claim 3, further comprising:
a flow guiding structure disposed in the overflow passage; the flow guiding structure being located at the inlet; and
a second cone structure cooperating with the flow guiding structure, the second cone structure being disposed on an end face, facing to the flow guiding structure, of the rotor assembly.

5. The blood pump device as claimed in claim 3, wherein the rotor assembly comprises a rotor and one or a plurality of vanes disposed on the rotor; when the rotor assembly comprises the plurality of vanes, the plurality of vanes are disposed at intervals around a circumferential direction of the rotor.

6. The blood pump device as claimed in claim 2, further comprising:
a flow guiding structure disposed in the overflow passage; the flow guiding structure being located at the inlet; and
a second cone structure cooperating with the flow guiding structure, the second cone structure being disposed on an end face, facing to the flow guiding structure, of the rotor assembly.

7. The blood pump device as claimed in claim 2, wherein the rotor assembly comprises a rotor and one or a plurality of vanes disposed on the rotor; when the rotor assembly comprises the plurality of vanes, the plurality of vanes are disposed at intervals around a circumferential direction of the rotor.

8. The blood pump device as claimed in claim 2, wherein the magnetic protection portion is made of a soft magnetic material.

9. The blood pump device as claimed in claim 1, wherein both the magnetic protection portion and the second permanent magnet portion are disposed on a side wall of the sleeve; the blood pump device further comprises:
a first non-magnetic portion disposed inside a rotor of the rotor assembly; and
a second non-magnetic portion disposed inside the side wall of the sleeve;
wherein, in a flowing direction of fluid, the first non-magnetic portion, the electric motor magnetic steel and the first permanent magnet portion are sequentially disposed at intervals, and the second non-magnetic portion, the coil and the second permanent magnet portion are sequentially disposed at intervals.

10. The blood pump device as claimed in claim 1, wherein a side wall of the sleeve comprises an inner wall and an outer wall disposed with the inner wall at interval; an annular space is formed between the inner wall and the outer wall, and the coil, the magnetic protection portion and the second permanent magnet portion are disposed in the annular space.

11. The blood pump device as claimed in claim 1, further comprising:
a flow guiding structure disposed in the overflow passage; the flow guiding structure being located at the inlet; the flow guiding structure comprises a plurality of flow guiding vanes, and the plurality of flow guiding vanes are disposed at intervals on an inner wall of a sleeve of the housing in a circumferential direction; and
a second cone structure cooperating with the flow guiding structure, the second cone structure being disposed on an end face, facing to the flow guiding structure, of the rotor assembly.

12. The blood pump device as claimed in claim 1, wherein in a flowing direction of fluid, an end face of the first permanent magnet portion facing the inlet is flush with an end face of the second permanent magnet portion facing the inlet, and an end face of the first permanent magnet portion away from the inlet is flush with an end face of the second permanent magnet portion away from the inlet.

13. The blood pump device as claimed in claim 1, wherein the rotor assembly comprises a rotor and one or a plurality of vanes disposed on the rotor; when the rotor assembly comprises the plurality of vanes, the plurality of vanes are disposed at intervals around a circumferential direction of the rotor.

14. The blood pump device as claimed in claim 1, wherein the magnetic protection portion is made of a soft magnetic material.

15. The blood pump device as claimed in claim 1, wherein the volute comprises a bottom wall, wherein a surface, facing towards the rotor assembly, of the bottom wall is arranged inclined; or a surface, facing towards the rotor assembly, of the bottom wall is a plane.

* * * * *